United States Patent
Thakkar et al.

(10) Patent No.: US 10,926,087 B2
(45) Date of Patent: Feb. 23, 2021

(54) SYSTEMS AND METHODS FOR INTRAVASCULAR CATHETER POSITIONING AND/OR NERVE STIMULATION

(71) Applicant: Lungpacer Medical Inc., Vancouver (CA)

(72) Inventors: Viral S. Thakkar, Chester Springs, PA (US); Douglas G. Evans, Downingtown, PA (US); Matthew J. Gani, Seattle, WA (US)

(73) Assignee: Lungpacer Medical Inc., Burnaby (CA)

( * ) Notice: Subject to any disclaimer, the term of this patent is extended or adjusted under 35 U.S.C. 154(b) by 0 days.

(21) Appl. No.: 16/802,711

(22) Filed: Feb. 27, 2020

(65) Prior Publication Data

US 2020/0188658 A1    Jun. 18, 2020

Related U.S. Application Data

(63) Continuation of application No. 16/222,299, filed on Dec. 17, 2018, which is a continuation of application
(Continued)

(51) Int. Cl.
*A61N 1/36* (2006.01)
*A61B 5/04* (2006.01)
(Continued)

(52) U.S. Cl.
CPC .............. *A61N 1/3601* (2013.01); *A61B 5/24* (2021.01); *A61B 5/287* (2021.01); *A61B 5/349* (2021.01);
(Continued)

(58) Field of Classification Search
None
See application file for complete search history.

(56) References Cited

U.S. PATENT DOCUMENTS

| 1,693,734 A | 12/1928 | Waggoner |
| 2,532,788 A | 12/1950 | Sarnoff |

(Continued)

FOREIGN PATENT DOCUMENTS

| CN | 1652839 A | 8/2005 |
| CN | 102143781 A | 8/2011 |

(Continued)

OTHER PUBLICATIONS

Antonica A., et al., "Vagal Control of Lymphocyte Release from Rat Thymus," Journal of the Autonomic Nervous System, Elsevier, vol. 48(3), Aug. 1994, pp. 187-197.
(Continued)

*Primary Examiner* — Brian T Gedeon
(74) *Attorney, Agent, or Firm* — Bookoff McAndrews, PLLC

(57) ABSTRACT

A method for positioning an intravascular catheter may include inserting the intravascular catheter into a venous system of a patient, wherein the catheter includes a plurality of electrodes, and multiple electrodes of the plurality of electrodes are configured to emit electrical signals; positioning a distal portion of the catheter in a first position; using one or more electrodes of the plurality of electrodes to acquire an ECG signal; based on the acquired ECG signal, adjusting the distal portion of the catheter to a second position different from the first position; identifying at least one first electrode of the plurality of electrodes to stimulate a first nerve; identifying at least one second electrode of the plurality of electrodes to stimulate a second nerve; and
(Continued)

stimulating at least one of the first and second nerves to cause a contraction of a respiratory muscle.

17 Claims, 7 Drawing Sheets

Related U.S. Application Data

No. 15/666,989, filed on Aug. 2, 2017, now Pat. No. 10,195,429.

(51) Int. Cl.

| | | |
|---|---|---|
| *A61N 1/05* | (2006.01) | |
| *A61B 5/042* | (2006.01) | |
| *A61B 5/0452* | (2006.01) | |
| *A61B 5/00* | (2006.01) | |
| *A61B 5/24* | (2021.01) | |
| *A61B 5/287* | (2021.01) | |
| *A61B 5/349* | (2021.01) | |

(52) U.S. Cl.
CPC .......... *A61B 5/4893* (2013.01); *A61N 1/0551* (2013.01)

(56) References Cited

U.S. PATENT DOCUMENTS

| | | |
|---|---|---|
| 2,664,880 A | 1/1954 | Nathaniel, Jr. |
| 3,348,548 A | 10/1967 | Chardack |
| 3,470,876 A | 10/1969 | Barchilon |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,143,872 A | 3/1979 | Havstad et al. |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | DiMarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,165,133 A | 12/2000 | Rapoport |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |

(56) References Cited

U.S. PATENT DOCUMENTS

| | | |
|---|---|---|
| 6,236,892 B1 | 5/2001 | Feler |
| 6,240,320 B1 | 5/2001 | Spehr et al. |
| 6,249,708 B1 | 6/2001 | Nelson et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,080,645 B2 | 7/2006 | Genger et al. |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |

(56) References Cited

U.S. PATENT DOCUMENTS

| | | |
|---|---|---|
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,511,303 B2 | 8/2013 | Djupesland |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 * | 11/2014 | Karamanoglu ...... A61N 1/3611 607/123 |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | McCabe et al. |
| 9,168,377 B2 | 10/2015 | Hoffer |
| 9,174,046 B2 | 11/2015 | Francois et al. |
| 9,199,075 B1 | 12/2015 | Westlund |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,468,755 B2 | 10/2016 | Westlund |
| 9,474,894 B2 | 10/2016 | Mercanzini et al. |
| 9,485,873 B2 | 11/2016 | Shah et al. |
| 9,498,625 B2 | 11/2016 | Bauer |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,239 B2 | 4/2017 | Francois et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,349 B2 | 8/2017 | Westlund et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,132 B2 | 5/2018 | Francois et al. |
| 9,956,396 B2 | 5/2018 | Young et al. |
| 9,968,785 B2 | 5/2018 | Hoffer et al. |
| 9,968,786 B2 | 5/2018 | Bauer |
| 9,987,488 B1 | 6/2018 | Gelfand et al. |
| 9,999,768 B2 | 6/2018 | Gelfand et al. |
| 10,022,546 B2 | 7/2018 | Hoffer et al. |
| 10,035,017 B2 | 7/2018 | Thakkar et al. |
| 10,039,920 B1 | 8/2018 | Thakkar et al. |
| 10,195,429 B1 | 2/2019 | Thakkar et al. |
| 10,293,164 B2 | 5/2019 | Nash et al. |
| 10,300,270 B2 | 5/2019 | Gelfand et al. |
| 10,315,035 B2 | 6/2019 | Bauer |
| 10,335,592 B2 | 7/2019 | Bauer et al. |
| 10,369,361 B2 | 8/2019 | Bauer et al. |

(56) References Cited

U.S. PATENT DOCUMENTS

| | | |
|---|---|---|
| 10,391,314 B2 | 8/2019 | Hoffer et al. |
| 10,406,366 B2 | 9/2019 | Westlund et al. |
| 10,406,367 B2 | 9/2019 | Meyyappan et al. |
| 10,413,203 B2 | 9/2019 | Saha et al. |
| 10,448,995 B2 | 10/2019 | Olson |
| 10,493,271 B2 | 12/2019 | Bauer |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0024222 A1 | 10/2006 | Bradley et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2009/0318993 A1 | 12/2009 | Eidenschink et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0135553 A1 | 6/2010 | Joglekar |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2011/0301471 A1 | 12/2011 | Kwok et al. |
| 2012/0035684 A1 | 2/2012 | Thompson et al. |

(56) References Cited

U.S. PATENT DOCUMENTS

| | | |
|---|---|---|
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0296738 A1 | 10/2014 | Johnson et al. |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1* | 1/2016 | Gelfand ............... A61B 5/0826 607/42 |
| 2016/0059017 A1 | 3/2016 | Moffitt et al. |
| 2016/0129244 A1 | 5/2016 | Westlund |
| 2016/0144078 A1 | 5/2016 | Young et al. |
| 2016/0166831 A9 | 6/2016 | Cho et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0354607 A1 | 12/2016 | Masson et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021163 A1 | 1/2017 | Westlund et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326354 A1 | 11/2017 | Westlund et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |
| 2018/0256440 A1 | 9/2018 | Francois et al. |
| 2018/0280692 A1 | 10/2018 | Gelfand et al. |
| 2018/0326209 A1 | 11/2018 | Gelfand et al. |
| 2019/0247656 A1 | 8/2019 | Bauer |
| 2019/0255322 A1 | 8/2019 | Bauer et al. |
| 2019/0351229 A1 | 11/2019 | Westlund et al. |

FOREIGN PATENT DOCUMENTS

| | | | |
|---|---|---|---|
| EP | 0993840 | A1 | 4/2000 |
| EP | 1304135 | A2 | 4/2003 |
| EP | 0605796 | B1 | 8/2003 |
| EP | 2489395 | A1 | 8/2012 |
| FR | 2801509 | A1 | 6/2001 |
| JP | H08510677 | A | 11/1996 |
| JP | 2003503119 | A | 1/2003 |
| JP | 2010516353 | A | 5/2010 |
| JP | 2011200571 | A | 10/2011 |
| JP | 2012000195 | A | 1/2012 |
| WO | WO-9407564 | A2 | 4/1994 |
| WO | WO-9508357 | A1 | 3/1995 |
| WO | WO-9964105 | A1 | 12/1999 |
| WO | WO-9965561 | A1 | 12/1999 |
| WO | WO-0100273 | A1 | 1/2001 |
| WO | WO-02058785 | A1 | 8/2002 |
| WO | WO-03005887 | A2 | 1/2003 |
| WO | WO-03094855 | A1 | 11/2003 |
| WO | WO-2005018524 | A2 | 3/2005 |
| WO | WO-2006063339 | A2 | 6/2006 |
| WO | WO-2006110338 | A1 | 10/2006 |
| WO | WO-2006115877 | A1 | 11/2006 |
| WO | WO-2007053508 | A1 | 5/2007 |
| WO | WO-2008092246 | A1 | 8/2008 |
| WO | WO-2008094344 | A1 | 8/2008 |
| WO | WO-2009006337 | A1 | 1/2009 |
| WO | WO-2009134459 | A2 | 11/2009 |
| WO | WO-2010029842 | A1 | 3/2010 |
| WO | WO-2010148412 | A1 | 12/2010 |
| WO | WO-2011094631 | A1 | 8/2011 |
| WO | WO-2011158410 | A1 | 12/2011 |
| WO | WO-2012106533 | A2 | 8/2012 |
| WO | WO-2013131187 | A1 | 9/2013 |
| WO | WO-2013188965 | A1 | 12/2013 |
| WO | WO-2014008171 | A1 | 1/2014 |
| WO | WO-2015075548 | A1 | 5/2015 |
| WO | WO-2015109401 | A1 | 7/2015 |
| WO | WO-2019154834 | A1 | 8/2019 |
| WO | WO-2019154837 | A1 | 8/2019 |
| WO | WO-2019154839 | A1 | 8/2019 |

OTHER PUBLICATIONS

Ayas N. T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual

(56) References Cited

OTHER PUBLICATIONS

Meeting of Professional Research Scientists: Experimental Biology 2000, Abstract 97.9, Apr. 15-18, 2000.
Borovikova L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.
Borovikova L.V., et al., "Vagus Nerve Stimulation Attenuates the Systemic Inflammatory Response to Endotoxin," Nature, Macmillan Magazines Ltd, vol. 405, May 25, 2000, pp. 458-462.
Chinese Search Report for Application No. CN2013/80023357.5, dated Jul. 24, 2015.
Co-pending U.S. Appl. No. 15/606,867, filed May 26, 2017.
Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.
Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.
De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
Escher, Doris J.W. et al., "Clinical Control of Respiration by Transvenous Phrenic Pacing," American Society for Artificial Internal Organs: Apr. 1968—vol. 14—Issue 1—pp. 192-197.
European Search Report for Application No. 13758363, dated Nov. 12, 2015.
European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Huffman, William J. et al., "Modulation of Neuroinflammation and Memory Dysfunction Using Percutaneous Vagus Nerve Stimulation in Mice," Brain Stimulation, 2018.
Ishii, K. et al., "Effects of Bilateral Transvenous Diaphragm Pacing on Hemodynamic Function in Patients after Cardiac Operations," J. Thorac. Cardiovasc. Surg., 1990.

Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, ELSEVIER, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lungpacer: Therapy, News.< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35(1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.

(56) References Cited

OTHER PUBLICATIONS

Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.

Scheinman R.I., et al., "Role of Transcriptional Activation of IκBα in Mediation of Immunosuppression by Glucocorticoids," Science, vol. 270, Oct. 13, 1995, pp. 283-286.

Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.

Steinlein, O., "New Functions for Nicotinic Acetylcholine Receptors?," Behavioural Brain Research, vol. 95, 1998, pp. 31-35.

Sternberg E.M., (Series Editor) "Neural-Immune Interactions in Health and Disease," The Journal of Clinical Investigation, vol. 100 (11), Dec. 1997, pp. 2641-2647.

Sykes., A.P., et al., "An Investigation into the Effect and Mechanisms of Action of Nicotine in Inflammatory Bowel Disease," Inflammation Research, vol. 49, 2000, pp. 311-319.

Toyabe S., et al., "Identification of Nicotinic Acetylcholine Receptors on Lymphocytes in the Periphery as well as Thymus in Mice," Immunology, vol. 92, 1997, pp. 201-205.

Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.

Wanner, A. et al., "Trasvenous Phrenic Nerve Stimulation in Anesthetized Dogs," Journal of Applied Physiology, 1973, vol. 34 (4), pp. 489-494.

Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

PCT Search Report and Written Opinion dated Oct. 17, 2018 for PCT Application No. PCT/US2018/043661, 13 pages.

\* cited by examiner

SYSTEMS AND METHODS FOR INTRAVASCULAR CATHETER POSITIONING AND/OR NERVE STIMULATION

CROSS-REFERENCE TO RELATED APPLICATIONS

This application is a continuation of U.S. application Ser. No. 16/222,299, filed Dec. 17, 2018, which is a continuation of U.S. application Ser. No. 15/666,989, filed Aug. 2, 2017, now U.S. Pat. No. 10,195,429, both of which are hereby incorporated by reference.

TECHNICAL FIELD

This disclosure relates to systems, devices, and methods for one or more of positioning an intravascular nerve stimulation catheter, selecting electrodes for nerve stimulation, or stimulating nerves.

BACKGROUND

Electrical stimulation of nerves may be used to control muscle activity or to generate or attenuate sensations. Nerves and muscles may be stimulated by placing electrodes in, around, or near the nerves and muscles and by activating the electrodes by means of an implanted or external source of energy (e.g., electricity).

The diaphragm muscle provides an important function for the respiration of human beings. The phrenic nerves normally transmit signals from the brain to cause the contractions of the diaphragm muscle necessary for breathing. However, various conditions can prevent appropriate signals from being delivered to the phrenic nerves. These include: permanent or temporary injury or disease affecting the spinal cord or brain stem; Amyotrophic Lateral Sclerosis (ALS); decreased day or night ventilatory drive (e.g., central sleep apnea, Ondine's curse); and decreased ventilatory drive while under the influence of anesthetic agents and/or mechanical ventilation. These conditions affect a significant number of people.

Intubation and positive pressure mechanical ventilation (MV) may be used for periods of several hours or several days, sometimes weeks, to help critically ill patients breathe while in intensive care units (ICU). Some patients may be unable to regain voluntary breathing and thus require prolonged or permanent mechanical ventilation. Although mechanical ventilation can be initially lifesaving, it has a range of significant problems and/or side effects. Mechanical ventilation:

- often causes ventilator-induced lung injury (VILI) and alveolar damage, which can lead to accumulation of fluid in the lungs and increased susceptibility to infection (ventilator-associated pneumonia, VAP);
- commonly requires sedation to reduce discomfort and anxiety in acutely intubated patients;
- leads to rapid atrophy of the disused diaphragm muscle (ventilator-induced diaphragm dysfunction, VIDD);
- can adversely affect venous return because the lungs are pressurized and the diaphragm is inactive;
- interferes with eating and speaking;
- requires apparatus that is not readily portable; and
- increases the risk of dying if the patient fails to regain normal breathing and becomes ventilator-dependent.

A patient who is sedated and connected to a mechanical ventilator cannot breathe normally because the central neural drive to the diaphragm and accessory respiratory muscles are suppressed. Inactivity leads to muscle disuse atrophy and an overall decline in well-being. Diaphragm muscle atrophy occurs rapidly and can be a serious problem to the patient. According to a published study of organ donor patients (Levine et al., New England Journal of Medicine, 358: 1327-1335, 2008), after only 18 to 69 hours of mechanical ventilation, all diaphragm muscle fibers had shrunk on average by 52-57%. Muscle fiber atrophy results in muscle weakness and increased fatigability. Therefore, ventilator-induced diaphragm atrophy could cause a patient to become ventilator-dependent. It has been estimated that over 600,000 U.S. patients will be ventilator-dependent and require prolonged mechanical ventilation by the year 2020. Zilberberg et al., "Growth in adult prolonged acute mechanical ventilation: implications for healthcare delivery," Crit Care Med., 2008 May, 36(5): 1451-55.

SUMMARY

Embodiments of the present disclosure relate to, among other things, systems, devices, and methods for one or more of positioning an intravascular nerve stimulation catheter, selecting electrodes for nerve stimulation, or stimulating nerves. Each of the embodiments disclosed herein may include one or more of the features described in connection with any of the other disclosed embodiments.

In one example, a method for positioning an intravascular catheter may include inserting the intravascular catheter into a venous system of a patient, wherein the catheter includes a plurality of electrodes, and multiple electrodes of the plurality of electrodes are configured to emit electrical signals; positioning a distal portion of the catheter in a first position; using one or more electrodes of the plurality of electrodes to acquire an ECG signal; based on the acquired ECG signal, adjusting the distal portion of the catheter to a second position different from the first position; identifying at least one first electrode of the plurality of electrodes to stimulate a first nerve; identifying at least one second electrode of the plurality of electrodes to stimulate a second nerve; and stimulating at least one of the first and second nerves to cause a contraction of a respiratory muscle.

Any method described herein may additionally or alternatively include one or more of the following features or steps: inserting the intravascular catheter into the venous system may include inserting the intravascular catheter into: 1) at least one of a left subclavian, axillary, cephalic, cardiophrenic, brachial, radial, or left jugular vein, and 2) a superior vena cava; the first position may be proximate an atrium of a heart of the patient, and the second position may be in a superior vena cava; the ECG signal may be a first ECG signal, and the method may further comprise using one or more electrodes of the plurality of electrodes to acquire a second ECG signal; the one or more electrodes used to acquire the first ECG signal may be positioned on a proximal portion of the catheter and may be configured to stimulate the first nerve, and the one or more electrodes used to acquire the second ECG signal may be positioned on a distal portion of the catheter and may be configured to stimulate the second nerve; the method may further include comparing the first ECG signal to the second ECG signal, and based on the comparison, adjusting the distal portion of the catheter to the second position; the second position may be farther from a heart of the patient than the first position; the method may further include using one or more electrodes of the plurality of electrodes to sense at least one of an impedance or nerve activity; or each of the at least one first electrode and the at least one second electrode may be a combination of electrodes.

In another example, a method for positioning an intravascular catheter may include inserting the intravascular catheter into: 1) at least one of a left subclavian vein or a left jugular vein, and 2) a superior vena cava, wherein the catheter includes a plurality of electrodes, and the plurality of electrodes includes a proximal set of electrodes positioned proximate a left phrenic nerve and a distal set of electrodes positioned proximate a right phrenic nerve; using one or more electrodes of the plurality of electrodes to acquire an ECG signal; based on a change in the ECG signal, withdrawing the catheter away from a heart of a patient; stimulating the left phrenic nerve using one or more electrodes of the proximal set of electrodes; and stimulating the right phrenic nerve using one or more electrodes of the distal set of electrodes.

Any method described herein may additionally or alternatively include one or more of the following features or steps: the change in the ECG signal may be a change in an amplitude of a P-wave, and the change may occur as a distal end of the catheter enters a region proximate an atrium of the heart; the step of withdrawing the catheter away from the heart may cause a change in the amplitude of the P-wave; the ECG signal may be a first ECG signal acquired by one or more electrodes of the proximal set of electrodes, and the method may further include using one or more electrodes of the distal set of electrodes to acquire a second ECG signal; the method may further include determining a difference between a P-wave of the first ECG signal and a P-wave of the second ECG signal, and withdrawing the catheter away from the heart of the patient when the difference exceeds a predetermined value; the difference may exceed the predetermined value when the catheter is advanced into an atrium of the heart; a hub coupled to the catheter and positioned exterior to the patient may be used with the one or more electrodes of the plurality of electrodes to acquire the ECG signal; or the method may further include monitoring the ECG signal as a distal end of the catheter is inserted into the at least one of the left subclavian vein or the left jugular vein and advanced into the superior vena cava.

In yet another example, a method for positioning an intravascular catheter may include inserting the intravascular catheter into a venous system of a patient, wherein the catheter includes a plurality of proximal electrodes and a plurality of distal electrodes; using one or more electrodes of the plurality of proximal electrodes to acquire a first ECG signal, and using one or more electrodes of the plurality of distal electrodes to acquire a second ECG signal; comparing the first ECG signal to the second ECG signal; based on the comparison between the first ECG signal and the second ECG signal, adjusting a position of the catheter; stimulating the first nerve using one or more of the plurality of proximal electrodes; and stimulating the second nerve using one or more of the plurality of distal electrodes.

Any method described herein may additionally or alternatively include one or more of the following features or steps: the first nerve may be a left phrenic nerve, and the second nerve may be a right phrenic nerve; comparing the first ECG signal to the second ECG signal may include comparing an amplitude of a portion of the first ECG signal to an amplitude of a portion of the second ECG signal; the step of comparing may occur a plurality of times during the inserting step; adjusting the position of the catheter may include moving the catheter away from a heart; at least one of stimulating the first nerve or stimulating the second nerve may cause a contraction of a diaphragm; or the method may further include sensing activity of the first nerve using one or more of the proximal electrodes and sensing activity of the second nerve using one or more of the distal electrodes In another example, a method for positioning an intravascular catheter may include inserting the intravascular catheter into: 1) at least one of a left subclavian vein or a left jugular vein, and 2) a superior vena cava, wherein the catheter includes a plurality of proximal electrodes configured to be positioned proximate a left phrenic nerve and a plurality of distal electrodes configured to be positioned proximate a right phrenic nerve; at multiple positions of the catheter during the inserting step, using one or more electrodes of the plurality of proximal electrodes to acquire a first ECG signal, and using one or more electrodes of the plurality of distal electrodes to acquire a second ECG signal; comparing the first ECG signal to the second ECG signal at several of the multiple positions; based on the comparisons of the first ECG signal to the second ECG signal, determining a desired position of the catheter for nerve stimulation; stimulating the left phrenic nerve using one or more of the plurality of proximal electrodes; and stimulating the right phrenic nerve using one of more of the plurality of distal electrodes.

Any method described herein may additionally or alternatively include one or more of the following features or steps: the method may further include advancing a distal end of the catheter into a region proximate an atrium of a heart; one of the multiple positions may be a position in which the distal end of the catheter is proximate the atrium of the heart, and in the position, the comparison may indicate a difference between an amplitude of the first ECG signal and an amplitude of the second ECG signal that exceeds a predetermined value; the method may further include moving the catheter away from the heart; stimulating the left phrenic nerve may cause a diaphragm contraction, and stimulating the right phrenic nerve may cause a diaphragm contraction; the proximal electrodes used to acquire the first ECG signal may be configured to stimulate the left phrenic nerve, and the distal electrodes used to acquire the second ECG signal may be configured to stimulate the right phrenic nerve.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

When electrically stimulating nerves or muscles, a variety of goals may be considered. First, it may be desirable to place the electrodes in proximity to the phrenic nerves. Second, it may be desirable to avoid placing electrodes in close proximity to the sinoatrial (SA) node, atrioventricular (AV) node, or the His-Purkinje system located in heart tissue, as electrical stimulation of these anatomical features may cause arrhythmia. Third, when using a device that includes multiple electrodes, it may be desirable to identify particular electrodes that are in close proximity to the nerve. Identifying the proper electrodes may minimize the electrical charge required to effectively stimulate the nerves. Finally, as with any medical procedure, the risk of injury to the patient increases with the length and complexity of the medical procedure. Accordingly, it may be desirable to minimize the length of any procedure to electrically stimulate nerves or muscles.

There remains a need for cost-effective, practical, surgically simple, and minimally invasive devices and methods that address one or more of the above goals and can include one or more of a variety of functions, including: determining whether a nerve is the target nerve, stimulating breathing, delivering treatment (e.g., medications), sensing electrical signals from the body (e.g., ECG), sensing internal vascular blood pressure, heart rate, and electrical impedance, and performing tests, such as detecting respiration rate and blood gas levels (e.g, $CO_2$, $O_2$). There is also a need for devices and methods to help patients wean from mechanical ventilation and regain the ability to breathe naturally.

Accordingly, the present disclosure is drawn to systems, devices, and methods for one or more of positioning an intravascular catheter for nerve stimulation, selecting electrodes for nerve stimulation, and stimulating nerves. In particular, embodiments of the present disclosure may use various positioning features to obtain information useful for positioning a transvascular nerve stimulation catheter, or may use information gathered by sensors to select electrodes and parameters for nerve stimulation.

General System Overview

Figure 1:
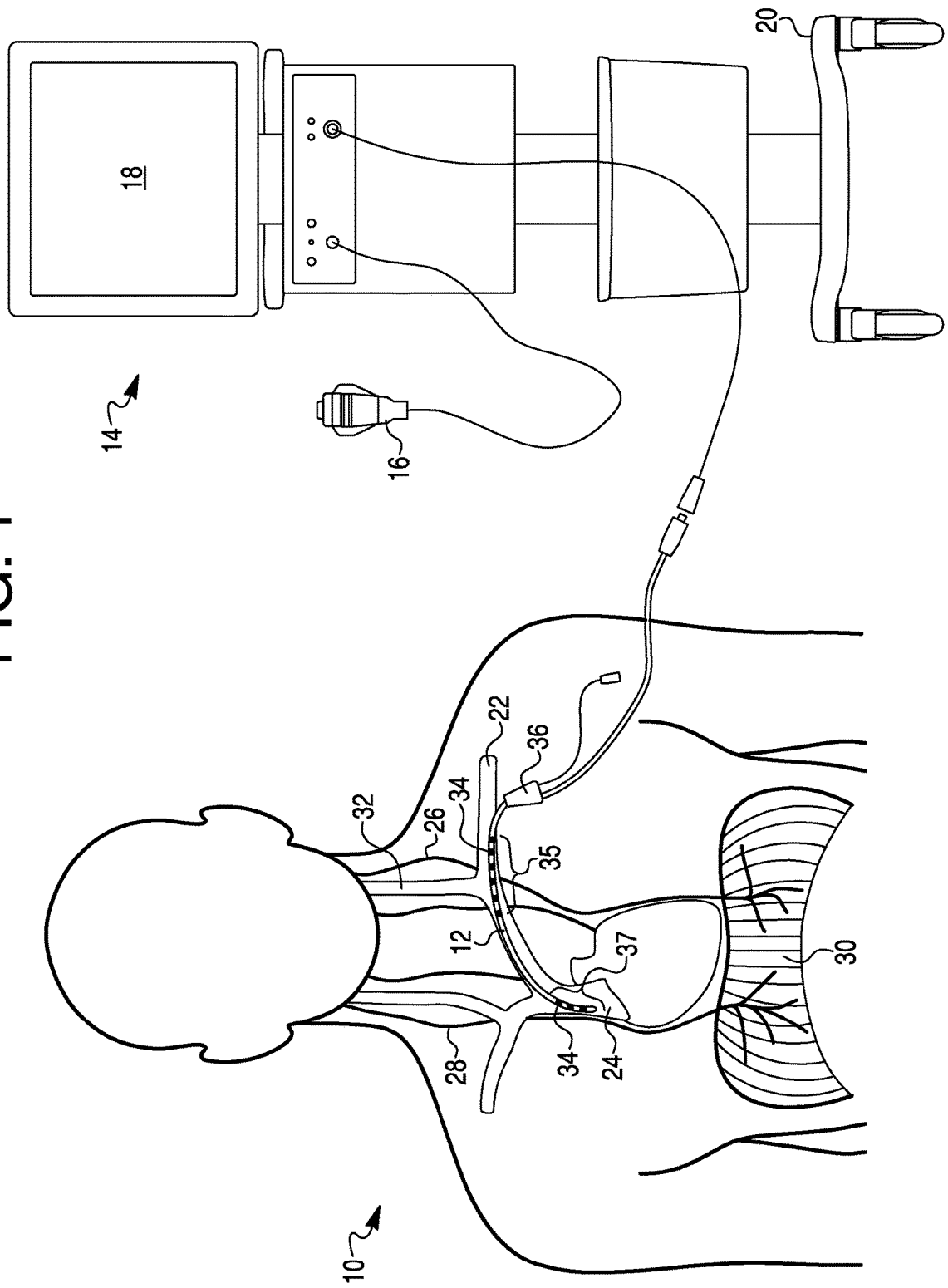
FIG. 1 illustrates a nerve stimulation system with an intravascular catheter positioned within a patient, according to an exemplary embodiment.

FIG. 1 illustrates a system 10 that includes a transvascular nerve stimulation catheter 12 and a control unit 14. Catheter 12 may include a plurality of electrodes 34. Catheter 12 may be operably connected (e.g., hardwired, wireless, etc.) to a control unit 14. The control unit 14 may be programmed to perform any of the functions described herein in connection with system 10. In some embodiments, the control unit 14 may include a remote controller 16 to allow a patient or health professional to control operation of the control unit 14 at a distance from the control unit 14. The controller 16 may include a handheld device, as illustrated in FIG. 1. In some examples, controller 16 may include a footswitch/pedal, a voice-activated, touch-activated, or pressure-activated switch, or any other form of a remote actuator. The control unit 14 may include a touch screen 18 and may be supported by a cart 20.

During use, a proximal portion of catheter 12 may be positioned in a left subclavian vein 22, and a distal portion of catheter 12 may be positioned in a superior vena cava 24. Positioned in this manner, electrodes 34 on the proximal portion of catheter 12 may be positioned proximate a left phrenic nerve 26, and electrodes 34 on the distal portion of catheter 12 may be positioned proximate a right phrenic nerve 28. Left and right phrenic nerves 26, 28 may innervate a diaphragm 30. Accordingly, catheter 12 may be positioned to electrically stimulate one or both of the left and right phrenic nerves 26, 28 to cause contraction of the diaphragm muscle 30 to initiate or support a patient breath. In other embodiments, the proximal portion of catheter 12 may be positioned in a left jugular vein 32, and the distal portion of catheter 12 may be positioned in superior vena cava 24.

In further examples, catheter 12 can be placed into and advanced through other vessels providing access to the locations adjacent the target nerve(s) (e.g., phrenic nerves), such as: the jugular, axillary, cephalic, cardiophrenic, brachial, or radial veins. In addition, catheter 12 may use other forms of stimulation energy, such as ultrasound, to activate the target nerves. In some examples, the system 10 can target other respiratory muscles (e.g., intercostal) either in addition to, or alternatively to, the diaphragm 30. The energy can be delivered via one or more methods including transvascular, subcutaneous, nerve cuffs, transdermal stimulation, or other techniques known in the field.

Figure 2:
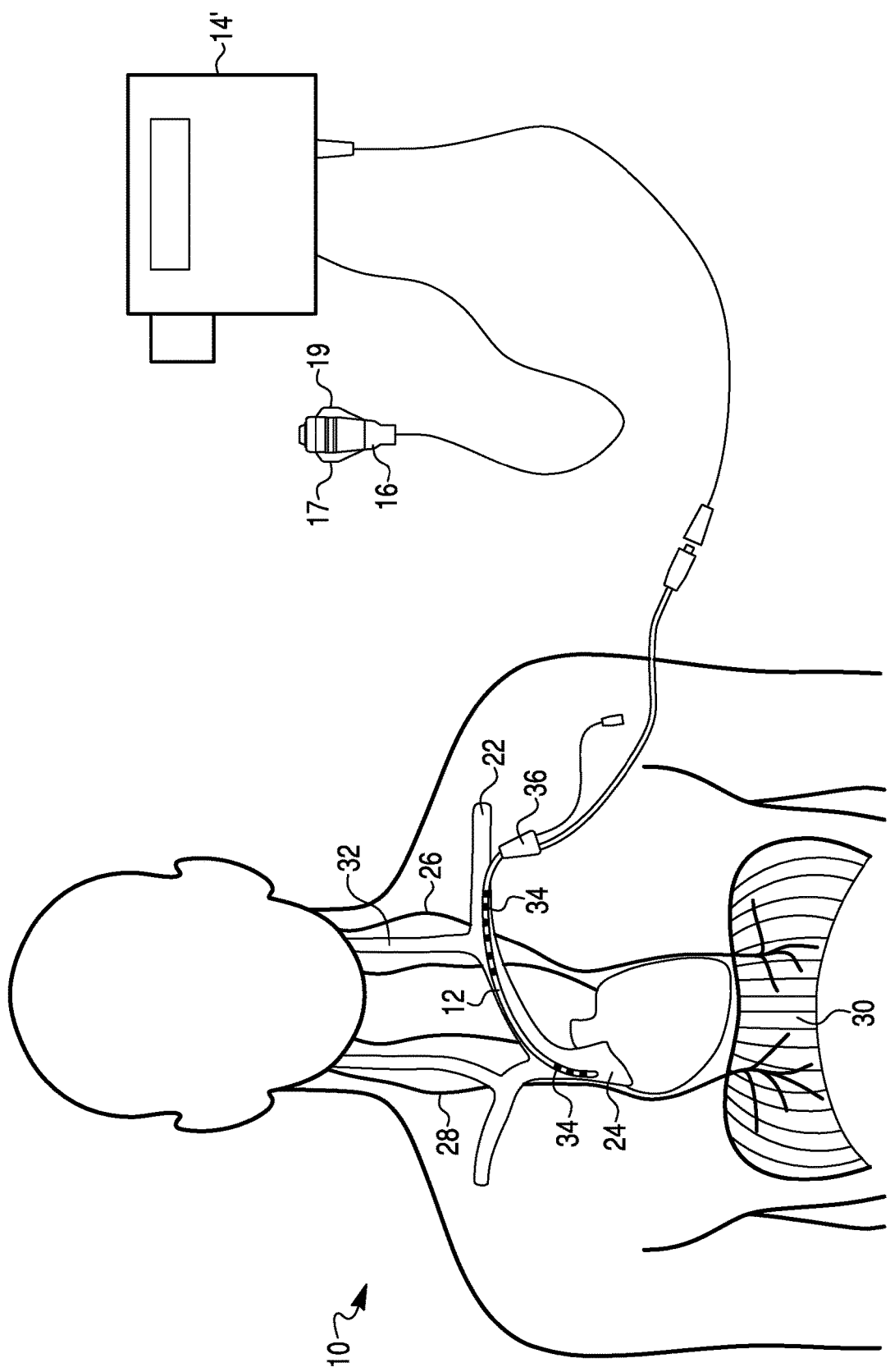
FIG. 2 illustrates a nerve stimulation system having a portable control unit, according to an exemplary embodiment.

FIG. 2 illustrates an alternative example of system 10, in which control unit 14' is portable. Portable control unit 14' may include all of the functionality of control unit 14 of FIG. 1, but it may be carried by a patient or other user to provide the patient with more mobility. In addition to carrying the control unit 14', the patient can wear control unit 14' on a belt, on other articles of clothing, or around his/her neck, for example. In other examples, control unit 14' may be mounted to a patient's bed to minimize the footprint of system 10 in the area around the patient, or to provide portable muscle stimulation in the event a bed-ridden patient needs to be transported or moved to another location.

Similar to FIG. 1, the system of FIG. 2 may include a controller 16, shown as a handheld controller 16. Handheld controller 16 may include buttons 17, 19 that can be pressed by a patient or other user to control breathing patterns. In one example, pressing one of buttons 17, 19 can initiate a "sigh" breath, which may cause a greater volume of air to enter the patient's lungs than in a previous breath. A sigh breath may result when electrodes 34 of catheter 12 are directed to stimulate one or more of the phrenic nerves 26, 28 at a higher level than a normal breath (i.e., a stimulation train having a longer duration of stimulation or having pulses with a higher amplitude, pulse width, or frequency). Higher amplitude stimulation pulses can recruit additional nerve fibers, which in turn can engage additional muscle fibers to cause stronger and/or deeper muscle contractions. Extended pulse widths or extended durations of the stimulation train can deliver stimulation over longer periods of time to extend the duration of the muscle contractions. In the case of diaphragm muscle stimulation, longer pulse widths have the potential to help expand the lower lung lobes by providing greater or extended negative pressure around the outside of the lungs. Such negative pressure has the potential to help prevent or mitigate a form of low pressure lung injury known as atelectasis. The increased stimulation of the one or more phrenic nerves 26, 28 may result in a more forceful contraction of the diaphragm 30, causing the patient to inhale a greater volume of air, thereby providing a greater amount of oxygen to the patient. Sigh breaths may increase patient comfort.

In other examples, buttons 17, 19 may allow the patient or other user to start and stop stimulation therapy, or to increase or decrease stimulation parameters, including stimulation charge (amplitude x pulse width), frequency of pulses in a stimulation train, or breath rate. LED indicators or a small LCD screen (not shown) on the controller may provide other information to guide or inform the operator regarding the stimulation parameters, the feedback from the system sensors, or the condition of the patient.

Figure 3:
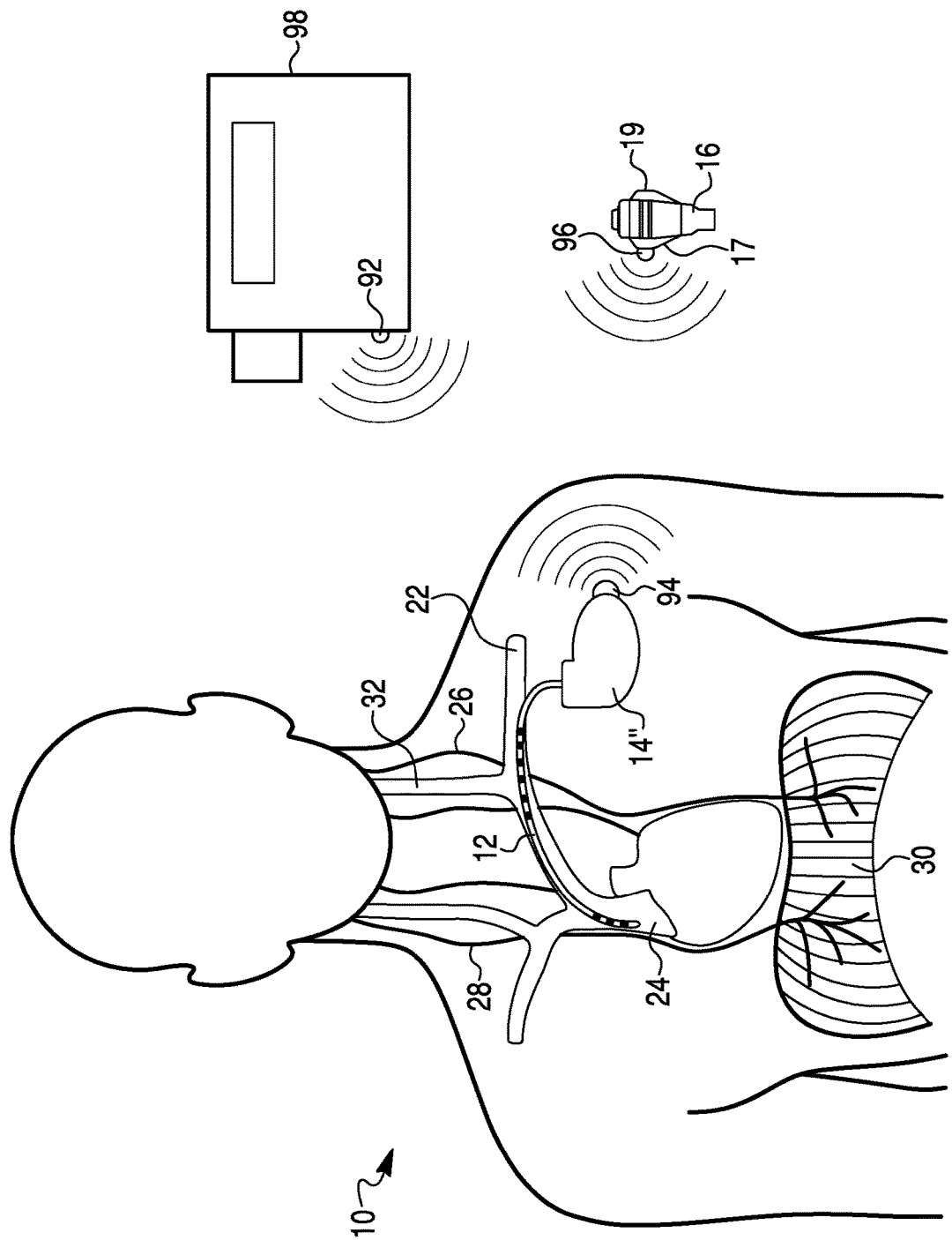
FIG. 3 illustrates a wireless configuration of a nerve stimulation system, according to an exemplary embodiment.

FIG. 3 illustrates another example of system 10 in which a control unit 14" is implanted in the patient, along with catheter 12. System 10 may further include remote controller 16 and a programmer 98 that communicates with control unit 14" wirelessly. In this embodiment, each of programmer 98, control unit 14", and remote controller 16 may include a wireless transceiver 92, 94, 96, respectively, so that each of the three components can communicate wirelessly with each other. Control unit 14" may include all of the electronics, software, and functioning logic necessary to perform the functions described herein. Implanting control unit 14" as shown in FIG. 3 may allow catheter 12 to function as a permanent breathing pacemaker. Programmer 98 may allow the patient or health professional to modify or otherwise program the nerve stimulation or sensing parameters. Remote controller 16 may be used as described in connection with FIGS. 1 and 2. In other examples, remote controller 16 may be in the form of a smartphone, tablet, watch or other wearable device.

Catheter Features

Referring to FIGS. 1-3, catheter 12 may include a stimulation array comprising a plurality of electrodes 34 or other energy delivery elements. In one example, electrodes 34 may be surface electrodes located on an outer wall of catheter 12. In another example, electrodes 34 may be positioned radially inward relative to the outer wall of catheter 12 (e.g., exposed through openings in the outer wall). In yet another example, the electrodes 34 may include printed electrodes as described in U.S. Pat. No. 9,242,088, which is incorporated by reference herein (see below).

Figure 5:
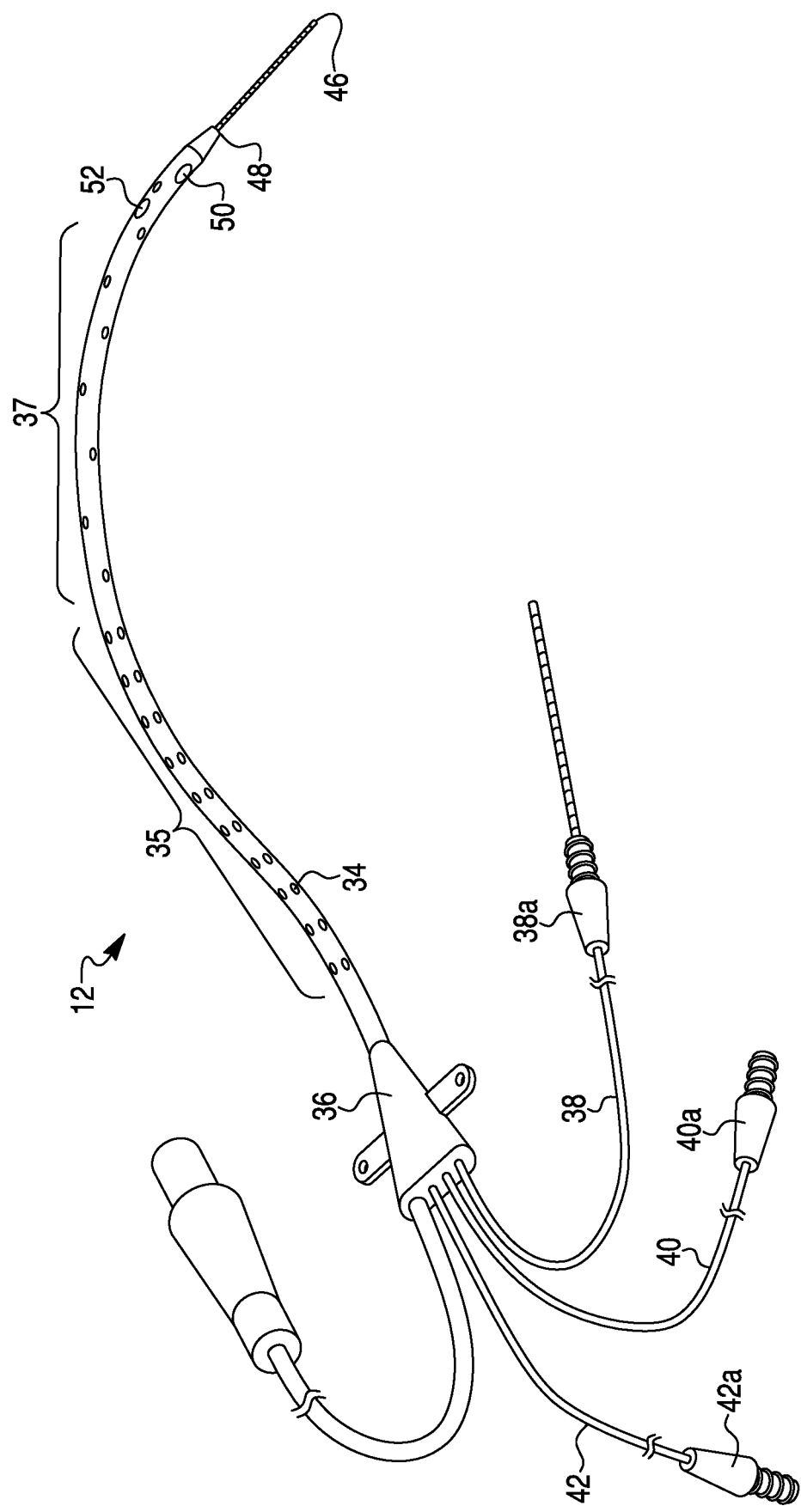
FIG. 5 illustrates an intravascular catheter having an optical fiber camera, according to an exemplary embodiment.

Electrodes 34 may extend partially around the circumference of catheter 12. This "partial" electrode configuration may allow electrodes 34 to target a desired nerve for stimulation, while minimizing application of electrical charge to undesired areas of the patient's anatomy (e.g., other nerves or the heart). As shown in FIG. 1, catheter 12 may include a proximal set 35 of electrodes 34 configured to be positioned proximate to and stimulate left phrenic nerve 26 and a distal set 37 of electrodes 34 configured to be positioned proximate to and stimulate right phrenic nerve 28. As shown in FIG. 5, electrodes 34 may be arranged in rows extending along the length of catheter 12. In one example, proximal set 35 may include two rows, and distal set 37 may include two rows.

Furthermore, the catheters described herein may include any features of the nerve stimulation devices described in the following documents, which are all incorporated by reference herein in their entireties: U.S. Pat. No. 8,571,662 (titled "Transvascular Nerve Stimulation Apparatus and Methods," issued Oct. 29, 2013); U.S. Pat. No. 9,242,088 (titled "Apparatus and Methods for Assisted Breathing by Transvascular Nerve Stimulation," issued Jan. 26, 2016); U.S. Pat. No. 9,333,363 (titled "Systems and Related Methods for Optimization of Multi-Electrode Nerve Pacing," issued May 10, 2016); U.S. application Ser. No. 14/383,285 (titled "Transvascular Nerve Stimulation Apparatus and Methods," filed Sep. 5, 2014); or U.S. application Ser. No. 14/410,022 (titled "Transvascular Diaphragm Pacing Systems and Methods of Use," filed Dec. 19, 2014). In addition, the control units described herein can have any of the functionality of the control units described in the above-referenced patent documents (e.g., the control units described herein can implement the methods of nerve stimulation described in the incorporated documents).

During nerve stimulation, one or more electrodes 34 may be selected from the proximal set 35 for stimulation of left phrenic nerve 26, and one or more electrodes 34 may be selected from the distal set 37 for stimulation of right phrenic nerve 28. Catheter 12 may stimulate nerves using monopolar, bipolar, or tripolar electrode combinations, or using any other suitable combination of electrodes 34. In some examples, a second or third stimulation array can be used to stimulate other respiratory muscles. When multiple nerves or muscles are being stimulated, the controller and sensors described herein may be used to coordinate stimulation to achieve the desired muscle activation, breath, or level of respiratory support.

Catheter 12 may further include one or more lumens. Each lumen may extend from a proximal end of catheter 12 to a distal end of catheter 12, or to a location proximate the distal end of catheter 12. The lumens may contain medical devices, such as a guidewire or an optical fiber camera. Furthermore, the one or more lumens may be used for any suitable purpose, such as drawing blood samples or providing a pathway for delivering medications into the patient. In some examples, lumens may contain or be fluidly connected to sensors, such as blood gas sensors or pressure sensors.

In this disclosure, the figures illustrating catheter 12 may each illustrate different features and different combinations of features. However, catheter 12 may include any combination of the features that are described herein. Accordingly, the features of catheter 12 are not limited to the specific combinations shown in the various figures.

Referring to FIG. 2, a hub 36 may be connected to the proximal end of catheter 12. Hub 36 may include a conductive surface and can act as a reference electrode during monopolar stimulation or sensing. In some embodiments, hub 36 may be sutured on a patient's skin. In addition, hub 36 may be used as an ECG electrode.

Figure 4:
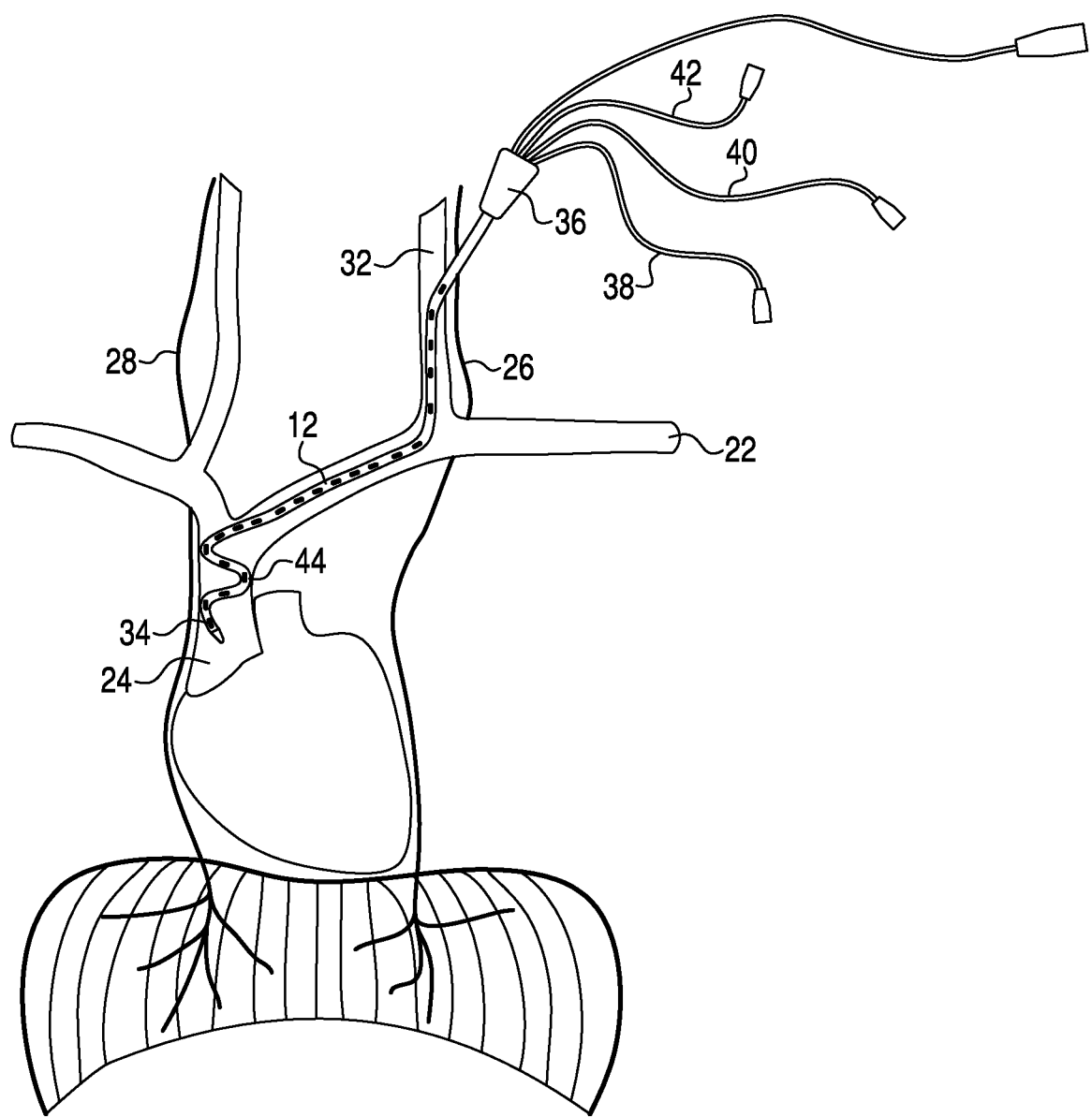
FIG. 4 illustrates an intravascular catheter having a helical portion, according to an exemplary embodiment.

FIG. 4 illustrates catheter 12 inserted into left jugular vein 32 and superior vena cava 24. As described above, catheter 12 includes a plurality of electrodes 34, with proximal electrodes 34 positioned near left phrenic nerve 26 and distal electrodes 34 positioned near right phrenic nerve 28. Catheter 12 may further include three lumens (not shown) that connect with extension lumens 38, 40, 42 that extend proximally from hub 36. The distal portion of catheter 12 may be configured to assume a helical shape 44 when positioned within the patient. Helical shape 44 may help anchor catheter 12 to the vessel wall to stabilize catheter 12 during nerve stimulation. Furthermore, helical shape 44 may allow electrodes 34 to be positioned at different radial positions within the vessel, which may be useful when selecting electrodes for nerve stimulation. For example, in certain instances it may be desirable to stimulate the nerve with electrodes 34 that are closer to the nerve (e.g., to obtain a stronger diaphragm response), and in other instances it may be desirable to stimulate the nerve with electrodes 34 that are farther away from the nerve (e.g., to obtain a weaker diaphragm response, or prevent stimulation of the vagus nerve).

In one example, helical shape 44 may be obtained by using a stiffening wire inserted into a lumen of catheter 12 via an extension lumen 38, 40, or 42. The stiffening wire may include a shape-memory material (e.g., Nitinol) biased to a helical shape, stainless steel, or any other suitable material. The portion of catheter 12 configured to assume the helical shape 44 may include materials having a lower stiffness than other portions of catheter 12. For example, the materials along helical shape 44 may be thinner or more flexible than the materials along the remaining length of catheter 12. In another example, catheter 12 may include a temperature-activated shape memory material (e.g., Nitinol) along a portion of its length, such that the shape-memory material of catheter 12 may have a substantially straight shape at room temperature and may assume a helical shape when heated within the patient's body.

In some examples, the proximal portion of catheter 12 additionally or alternatively may have a feature, similar to the distal portion of catheter 12, to allow it to assume a helical shape when positioned within left jugular vein 32 (or left subclavian vein 22). Any proximal helical shape may be obtained or result from any of the features described in connection with helical shape 44. If both the proximal and distal portions of catheter 12 assume a helical shape when positioned within the patient, both the proximal and distal electrodes 34 may be fixed relative to the left and right phrenic nerves 26, 28, respectively. To account for body movements when the patient breathes or moves, catheter 12 may further include a helical shape along a central portion of catheter 12. In one example, the diameter of an expanded helical shape in the central portion may be less than the diameter of the vessel wall, so that the central helical shape is not fixed relative to the vessel wall. Accordingly, the central helical portion may allow catheter 12 to freely expand and contract in length within the vessel as body movements cause the distance between the proximal helix and the distal helix (which may be fixed relative to the vessel walls) to vary. The central helical shape may be obtained or result from any of the features described in connection with helical shape 44.

Referring to FIG. 5, each of the extension lumens 38, 40, and 42 may end in a proximal-most port 38*a*, 40*a*, and 42*a*, respectively. Further, the lumens internal to catheter 12 may terminate in one or more distal ports. In one example, internal lumens that communicate with lumens 38, 40, and 42 terminate at a distal port 48, medial port 50, and proximal port 52, respectively. Lumens 38, 40, 42 and their corresponding internal lumens may be used to transport fluid to and from the patient, such as to deliver medications or withdraw blood or other bodily fluids. In other examples, these lumens may be used to hold a guidewire, stiffening wire, optical fiber camera, sensors, or other medical devices. FIG. 5 illustrates an optical fiber camera 46 inserted into lumen 38, extending through a corresponding internal lumen, and exiting from distal port 48.

Figure 6:
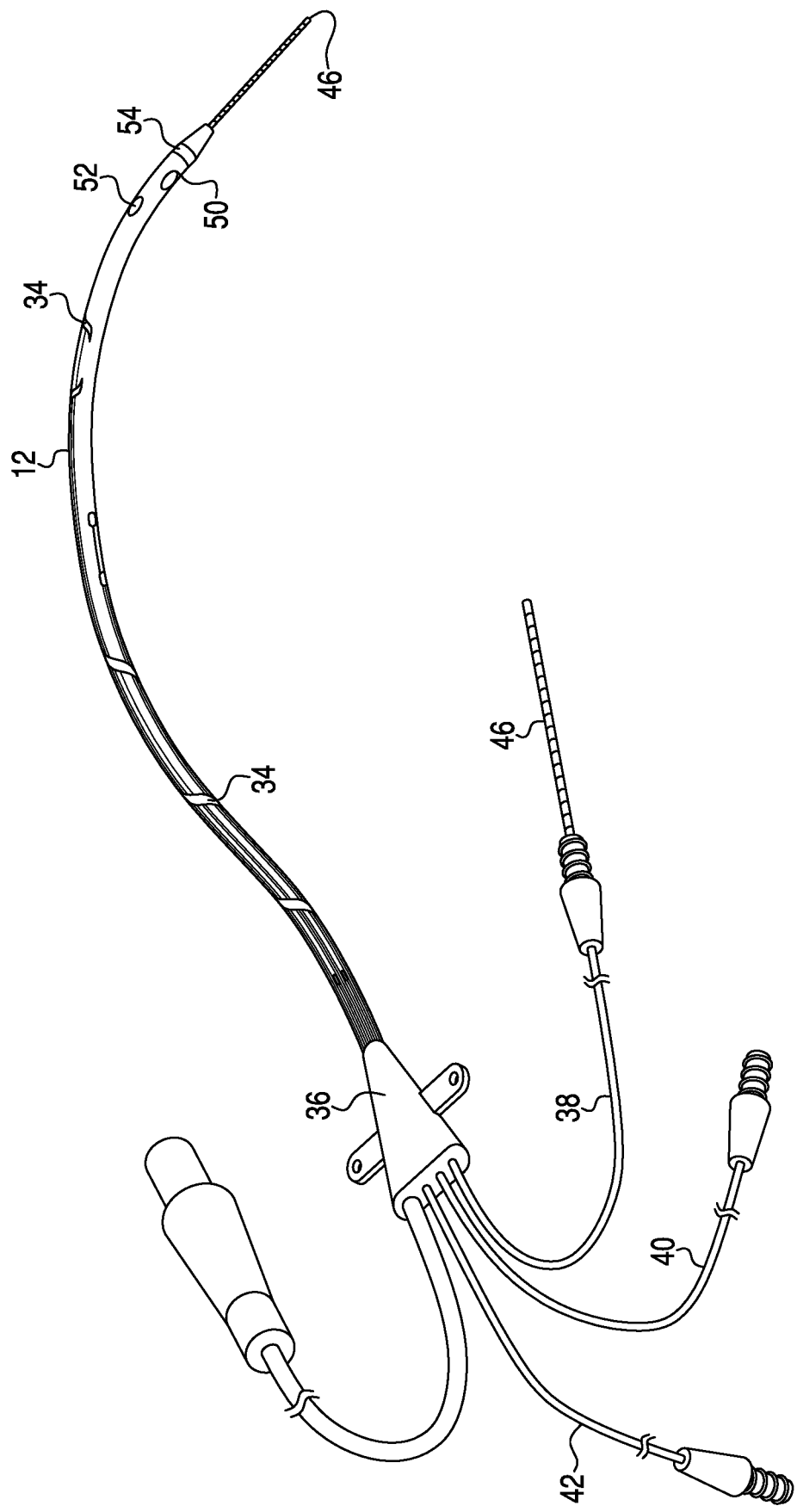
FIG. 6 illustrates an intravascular catheter having an ultrasound transducer, according to an exemplary embodiment.

FIG. 6 illustrates another example of catheter 12. Catheter 12 is similar to the catheter of FIG. 5, except electrodes 34 may be formed by conductive inks (such as silver, gold, graphine, or carbon flakes suspended in polymer or other media) printed on the surface of catheter 12, as described in U.S. Pat. No. 9,242,088, incorporated by reference herein (see above). These conductive inks may be deposited and adhered directly onto catheter 12 and sealed, except for the exposed electrodes 34, with an outer polyurethane or other flexible insulative film. The exposed electrodes 34 may be coated (e.g., with titanium nitride) for purposes such as one or more of: enhancing electrical properties, such as conductivity and surface area; providing corrosion resistance; and reducing the potential for formation of silver oxide, which could be toxic. As can be seen in FIG. 6, the conductive ink trace of distal electrodes may travel proximally along catheter 12 past the more proximal electrodes 34. FIG. 6 further illustrates catheter 12 having an ultrasound transducer 54 at a distal end of catheter 12, which will be described further below.

Detailed System Components

Figure 7:
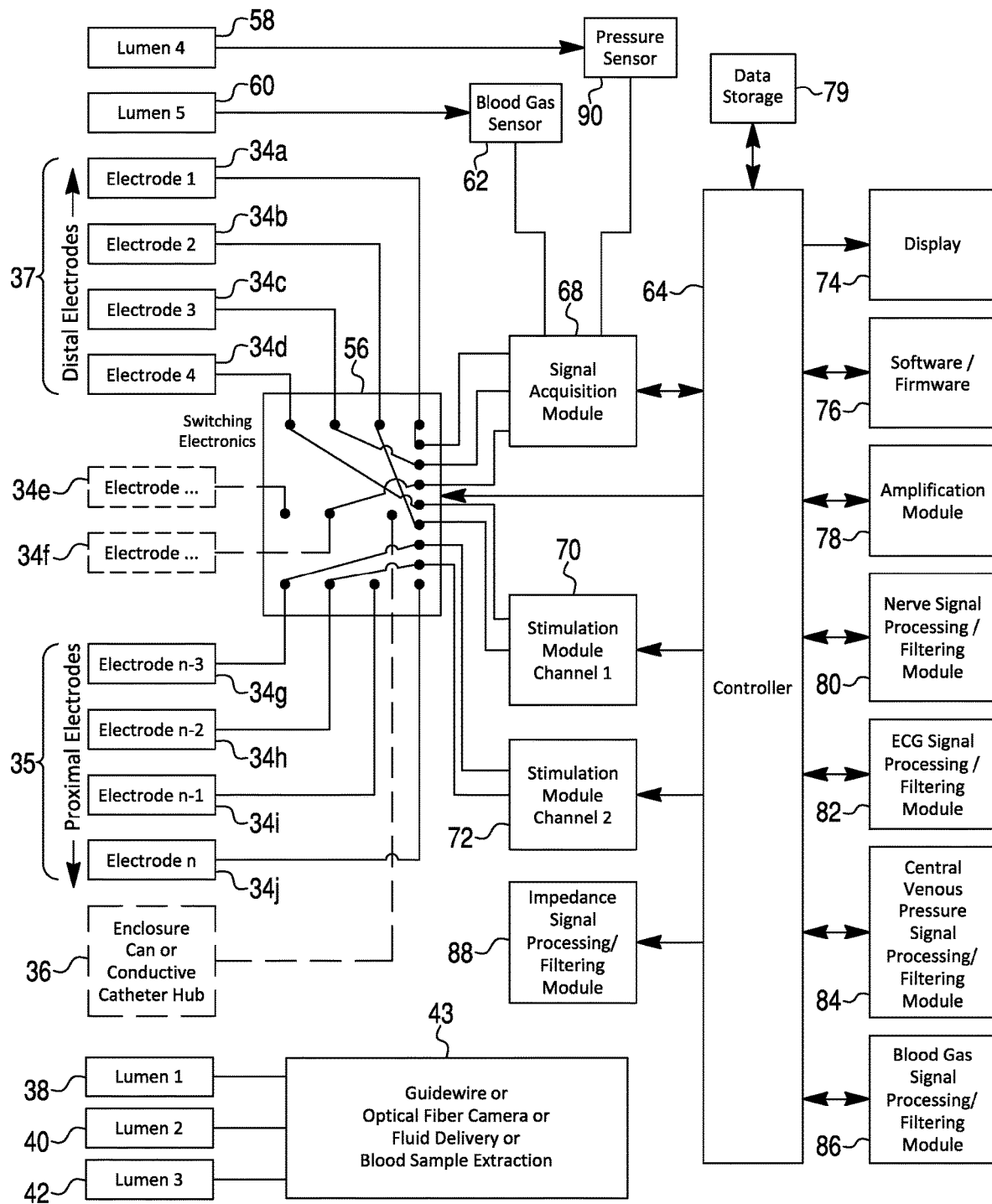
FIG. 7 illustrates a block diagram of a nerve stimulation system having an intravascular catheter and a control unit, according to an exemplary embodiment.

FIG. 7 illustrates a block diagram of the various components of system 10. The electrodes 34*a*-34*j*, hub 36, and lumens 38, 40, 42, 58, and 60 may be part of catheter 12 described herein. Catheter 12 may have any number of electrodes and any number of lumens. Five lumens are illustrated in FIG. 7, but in different examples, the catheter may include one, two, three, four, or more than five lumens. In one example, catheter 12 may have three lumens (e.g., extension lumens 38, 40, 42 and corresponding internal lumens), which each may hold one or more of a guidewire or optical fiber camera, or may be used for fluid delivery or blood sample extraction (box 43). In another example, catheter 12 may include four lumens, with one lumen 58 holding or fluidly connected to a pressure sensor 90, one lumen 60 holding or fluidly connected to a blood gas sensor 62, and the other two lumens holding a guidewire or optical fiber camera and/or being used for fluid delivery or blood sample extraction. It should be understood that any lumen of system 10 may contain or be fluidly connected to any of the devices (e.g., sensors, guidewire, optical fiber camera) described herein and/or may be used for any of the functions described herein (e.g., fluid delivery, blood sample extraction).

System 10 may include a controller 64, which may be part of any of the control units described herein. Each of the components of system 10 may be operably coupled to the controller 64, and controller 64 may manage operation of electrodes 34 during nerve stimulation, control the gathering of information by various sensors and electrodes 34, and control fluid delivery or extraction. It should be understood that the various modules described herein may be part of a computing system and are separated in FIG. 7 for explanatory purposes only; it is not necessary for the modules to be physically separate.

Electrodes 34*a*-34*j* may be electronically coupled to switching electronics 56, which may be communicably coupled to controller 64. As shown in FIG. 7, a portion of electrodes 34 may be distal electrodes 34*a*-34*d*, and a portion of electrodes 34 may be proximal electrodes 34*g*-34*j*. Other electrodes 34, such as electrodes 34*e* and 34*f*, may be positioned between the proximal and distal electrodes and, depending on the placement of catheter 12, may be used for stimulating either left or right phrenic nerves 26, 28. Hub 36 also may be connected to switching electronics 56 and may be used as an electrode.

Electrodes 34*a*-34*j* may be used for both electrically stimulating nerves and for gathering physiological information. When being used for nerve stimulation, a first combination of electrodes (e.g., one, two, three, or more electrodes) may be electrically coupled to a first stimulation module channel 70 for stimulation of a first nerve (e.g., the right phrenic nerve) and a second combination of electrodes (e.g., one, two, three, or more electrodes) may be electrically coupled to a second stimulation module channel 72 for stimulation of a second nerve (e.g., the left phrenic nerve).

Electrical signals may be sent from the first and second stimulation module channels 70, 72 to the electrode combinations to cause the electrodes to stimulate the nerves. In other examples, more than two electrode combinations (e.g., 3, 4, or more) may be used to stimulate one or more target nerves, and system 10 may include more than two stimulation module channels.

Electrodes 34a-34f may be further configured to sense physiological information from a patient, such as nerve activity, ECG, or electrical impedance, as will be described further below. When being used for sensing, one or more of electrodes 34a-34f may be electronically coupled to a signal acquisition module 68. Signal acquisition module 68 may receive signals from electrodes 34.

Switching electronics 56 may selectively couple electrodes 34 to first stimulation module channel 70, second stimulation module channel 72, or signal acquisition module 68. For example, if an electrode 34 (e.g., electrode 34a) is being used to acquire a signal, such as an ECG signal, that electrode 34 may be coupled via switching electronics 56 to signal acquisition module 68. Similarly, if a pair of electrodes (e.g., electrodes 34b and 34d) is being used to stimulate right phrenic nerve 28, those electrodes may be coupled via switching electronics 56 to first stimulation module channel 70. Finally, if a pair of electrodes (e.g., electrodes 34g and 34h) is being used to stimulate left phrenic nerve 26, those electrodes may be coupled via switching electronics 56 to second stimulation module channel 72. Switching electronics 56 may change which electrodes 34 are used for stimulation and which are used for sensing at any given time. In one example, any electrode 34 can be used for nerve stimulation and any electrode 34 can be used for sensing functions described herein. In other words, each electrode 34 may be configured to stimulate nerves, and each electrode 34 may be configured to sense physiological information.

Signal acquisition module 68 may further be coupled to one or more sensors configured to gather physiological information from a patient. For example, system 10 may include one or more of blood gas sensor 62 or pressure sensor 90. These sensors may be located in lumens of catheter 12, outside of the patient in fluid communication with a lumen, on an outer surface of catheter 12, or in any other suitable location. In one example, blood gas sensor 62 may be housed in or fluidly connected to lumen 60, while pressure sensor 90 may be housed in or fluidly connected to lumen 58. Blood gas sensor 62 may measure the amount of $O_2$ or $CO_2$ in the patient's blood. Pressure sensor 90 may measure the central venous pressure (CVP) of the patient.

Signal acquisition module 68 may transmit the signals received from one or more of electrodes 34, blood gas sensor 62, and/or pressure sensor 90 to the appropriate processing/filtering module of system 10. For example, signals from pressure sensor 90 may be transmitted to a central venous pressure signal processing/filtering module 84, where the signals are processed and filtered to aid in interpretation of CVP information. Similarly, signals from blood gas sensor 62 may be transmitted to a blood gas signal processing/filtering module 86 for processing and filtering to determine blood gas levels. Signals from electrodes 34, when they are used for sensing, may be sent to nerve signal processing/filtering module 80, ECG signal processing/filtering module 82, or impedance signal processing/filtering module 88, as appropriate. Signals from electrodes 34 or other sensors may be sent to amplification module 78, if necessary, to amplify the signals prior to being sent to the appropriate processing/filtering module.

Controller 64 may further communicate with display 74, which may serve as a user interface and may have a touch screen 18 (see FIG. 1). System 10 may further include software/firmware 76, which may contain the instructions necessary for carrying out the various functions described herein. Finally, system 10 may include data storage 79, for storing information gathered during sensing operations of catheter 12, and/or for storing instructions related to the operation of any of the modules or instructions for carrying out any of the functions described herein. Catheter 12 may contain unique identification features (e.g., RFID), and in the event the system 10 described herein (e.g., having one or more of controllers/programmers 14, 14', 14", 98, 64) is used to treat multiple patients concurrently, the catheter identification feature may allow the system 10 to uniquely identify each patient and access that patient's stored patient data.

Catheter Positioning

Catheter 12 may include a variety of positioning features that may help a user to position catheter 12 within a patient. Some positioning features may be visualization aids, such as optical fiber camera 46 shown in FIG. 5 or ultrasound transducer 54 shown in FIG. 6. Other positioning features may be sensors to sense physiological parameters, such as pressure sensor 90. Electrodes 34, which can be used to stimulate a nerve, also may be used as sensors to gather information that can then be used to position catheter 12. For example, electrodes 34 may gather information related to nerve activity (e.g., the left or right phrenic nerve), ECG signals, and/or impedance. Accordingly, a sensing electrode 34 may be considered a positioning feature. Each of the positioning features and how they are used to help position catheter 12 will be described in further detail below.

Catheter 12 may include any combination of positioning features, including one or more visualization aids, sensors (e.g., pressure), or electrodes capable of sensing various types of information. Similarly, the control units described herein, whether on a cart, wearable on a patient, or wireless, may be configured to process information gathered by the various positioning features described herein (e.g., visualization aids, sensors, and electrodes), as well as perform the various computerized functions described herein.

Referring back to FIG. 5, optical fiber camera 46 may be positioned within extension lumen 38 and its corresponding internal lumen within catheter 12, either temporarily or as an integral, permanent component of catheter 12. It should be understood that optical fiber camera 46 could be inserted into any of the extension lumens 38, 40, 42 and internal lumens, and could exit any of the ports 48, 50, 52. Optical fiber camera 46 may be used to aid in positioning of catheter 12 within the patient. For example, images from optical fiber camera 46 may be transmitted in real time to a health professional or other user during a procedure, who may rely on the images to guide catheter 12 through the patient's vessels and/or to adjust the position of the catheter within the vessels.

Referring back to FIG. 6, ultrasound transducer 54 may be used in addition to or instead of optical fiber camera 46 to obtain information useful for positioning catheter 12 within the patient. Ultrasound transducer 54 may be secured temporarily or permanently to the exterior of catheter 12, as shown in FIG. 6, or may be positioned temporarily or permanently within a lumen of catheter 12 (e.g., positioned to extend from the distal end of a lumen of catheter 12). Positioning ultrasound transducer 54 near the distal tip of catheter 12 may allow the user to view the inside of vessels and also ensure that the tip of catheter 12 is not positioned in an undesired location (e.g., in the atrium of the heart). For example, ultrasound transducer 54 may allow visualization of a heart valve, which could indicate that the catheter 12 has entered the atrium and may need to be retracted.

In addition to allowing a user to see the inside of the patient's vessels, the ultrasound images may provide information (e.g., calculated or visual) about the diameter of blood vessels and/or blood flow within the vessels. The user may then use vessel diameter information, blood flow, and real time images of the inside of the patient's vessels to position catheter 12 in a desired position.

CVP measurements from pressure sensor 90 may further aid in positioning catheter 12 within the patient. Normal values may vary between 4-12 cm H$_2$O. The CVP waveform may change based on the location, relative to the patient's heart, of the port (e.g., 46, 48, or 50) in communication with pressure sensor 90. In one example, CVP measurements may decline as the relevant port approaches the patient's heart. A user may read the changing CVP waveforms to help position the catheter 12 in a desired location relative to the patient's heart.

The CVP waveform has several components. The (a) wave corresponds to the right atrial contraction and correlates with the P wave on the ECG. The (c) wave corresponds to the cusp of the tricuspid valve protruding backwards through the atrium, as the right ventricle begins to contract. The (c) wave correlates with the end of the QRS complex on the ECG. The (x) descent corresponds to the movement of the right ventricle, which descends as it contracts. The downward movement decreases the pressure in the right atrium. At this stage, there is also atrial diastolic relaxation, which further decreases the right atrial pressure. The (x) descent happens before the T wave on the ECG. The (v) wave occurs as blood fills the right atrium and hits the tricuspid valve, causing a back-pressure wave. The (v) wave occurs after the T wave of the ECG. The (y) descent is a pressure decrease caused by the tricuspid valve opening in early ventricular diastole and occurs before the P wave of the ECG. The amplitudes of a, c, x, v, y may change depending on the position of the catheter with respect to the heart. The signature change of the CVP waveform can guide in the placement of catheter 12.

In one example, a method for positioning intravascular catheter 12 may include positioning catheter 12 in a first position in a venous system of a patient, wherein catheter 12 includes a plurality of electrodes 34 and at least one lumen extending from a proximal end of catheter 12 to a distal end of catheter 12, and each electrode 34 of the plurality of electrodes 34 is configured to emit electrical signals to stimulate a nerve; measuring a central venous pressure of the patient using a pressure sensor 90 fluidly connected to the at least one lumen; and based on the central venous pressure, adjusting catheter 12 to a second position different from the first position.

Nerve signals acquired by electrodes 34 also may be used to aid in positioning catheter 12 within a patient. The electrical signal from a nerve may be amplified by amplification module 78 and processed by nerve signal processing/filtering module 80. The amplified and filtered signals from one or more electrodes 34 then may be compared to an expected signal from the targeted nerve (e.g., left or right phrenic nerve) to identify electrodes 34 in close proximity to the target nerve and to identify the optimal one or more electrodes for nerve stimulation. For example, electrodes 34 returning a higher strength and/or higher quality signal may be located closer to the target nerve.

More specifically, phrenic nerve activity can be recorded using bipolar or monopolar electrodes. Phrenic nerve discharge can be amplified and filtered (e.g., 100 Hz to 5 kHz), and a moving average can be obtained using a third-order Paynter filter with a 20 or 50 ms time constant. Phrenic nerve discharge also can be filtered at 10 Hz to 5 kHz for analysis of spectral composition. A sampling rate of 1-10 kHz can be used to capture the nerve activity.

The parameters acquired during nerve activity sensing can be used to detect if the signal is from the phrenic nerve or another nerve. Sensed parameters can include a number of physiological parameters, such as amplitude, inspiration duration, and/or breathing rate. For example, if the sensed amplitude shows proximity of the electrodes 34 to the nerve and the nerve is a phrenic nerve, the duration of pulses in a train should match the sensed inspiration duration, and the frequency of the trains should match the sensed breathing rate. Furthermore, the sensed signals from a nerve can be compared to known nerve signatures (e.g., of phrenic nerves) to confirm that the nerve signal is from the desired nerve.

Electrodes 34 (e.g., two or three) may be used to acquire ECG signals, with hub 36 optionally being used as a reference electrode. The ECG signal (e.g., morphology, amplitudes, and spectral content) may vary depending on the location, relative to the patient's heart, of the electrodes being used to measure the signal. Monitoring changes in the ECG signal as catheter 12 is being positioned may aid in identifying desired or undesired placement. For example, it may be undesired for catheter 12 to be placed in the atrium of the patient's heart.

In one example, one of the distal electrodes 34 on catheter 12 may be designated as a probe. Other electrodes along the length of catheter 12, and in some cases in contact with the skin of the patient, may be used to detect an ECG signal, which can optionally be displayed by control unit 14 via screen 18. Catheter 12 may be advanced through superior vena cava 24 towards the heart. As catheter 12 enters a region proximate the right atrium, or enters the right atrium, the P-wave portion of the ECG may become elevated and create an augmented peaked P-wave, indicating that the tip of the catheter 12 lies in or very close to the right atrium. The operator can observe the change in P-wave, or the control unit 14 can utilize an algorithm to detect the change and provide a visual, audible or other signal to the operator. For example, an LED on catheter hub 36, control unit 14, or remote controller 16 can change from green to yellow and then to red as the P-wave changes indicate that the catheter 12 is approaching and then is positioned within the right atrium. The catheter 12 can then be withdrawn slowly until the P-wave starts to diminish. The catheter 12 can then be withdrawn a further 1-2 cm, thereby positioning the catheter tip in the distal portion of superior vena cava 24.

In this example, the positive deflection in the P-wave occurs when current flows to the probing electrode, and a negative deflection when it flows away. The P-wave depolarizes down the right atrium from the SA node, away from an electrode 34 in superior vena cava 24, and is therefore negative. The amplitude of the P-wave is related to the inverse square rule, whereby the amplitude is inversely proportional to the square of the distance from the current source. Thus, the P-wave increases greatly in negative amplitude as catheter 12 approaches the atrium. When the tip enters the atrium, it is just beyond the SA node, and the first portion of the P-wave depolarizes towards it. This results in a brief, small positive deflection followed instantly by a deep negative deflection.

Alternatively, a distal combination of electrodes 34 (e.g., a distal pair) and a proximal combinations of electrodes 34

(e.g., a proximal pair) can be used to obtain, respectively, a distal and proximal ECG signal having a P-wave. The P-waves can be compared using standard signal processing techniques and a delta value can be determined as the catheter 12 is advanced through the vessel (e.g. superior vena cava 24) towards the heart. As catheter 12 is advanced in close proximity to or into the atrium, the delta value will change significantly, exceeding a predetermined value. The system 10 can provide an indicator to the operator, as described previously, and catheter 12 can be withdrawn 1 to 2 cm. This method can also utilize one or more reference electrodes 34 located along the length of the catheter or positioned externally on the patient's body.

Electrodes 34 also may be used to measure impedance, which can provide information relevant to positioning catheter 12. Impedance may be measured between any two electrodes 34 of catheter 12. In one example, however, impedance may be measured between: a) either a proximal-most electrode 34 or hub 36, and b) a distal-most electrode.

The impedance presented to injected current may be dependent on the conductivity of the fluid, or adjacent tissue, in the local area between a pair of sensing electrodes 34. The conductivity further may depend on the cross-sectional area of the blood vessel at the site of the sending electrodes 34. The impedance of an electrode 34 may vary depending on the medium in which it is resting. For example, an electrode 34 placed in a relatively large body of conductive fluid may have a lower impedance than one resting against a vessel wall. The impedance of an electrode 34 can therefore be used to determine whether it is adjacent to a vessel wall or resting in a larger body of conductive fluid.

In one example, when catheter 12 is inserted into a patient, electrodes 34 that are on a proximal portion of catheter 12 may have a higher impedance than other electrodes 34, because the proximal portion of catheter 12 may be positioned in tissue (e.g., fatty) near an insertion site, rather than resting in the fluid of a blood vessel. Electrodes 34 farther down the shaft of catheter 12, towards a central portion of catheter 12, might have progressively lower impedances as the diameter of the vessel increases (e.g., as the vessel approaches superior vena cava 24). Electrodes 34 on the portion of catheter 12 that is floating in fluid in superior vena cava 24 might have a low impedance. Electrodes 34 on the distal portion of catheter 12, at or near the tip of catheter 12, might be in direct contact with the vessel wall and therefore may have a higher impedance. A graph of the impedances of all of the electrodes 34 in this example may have a U-shaped curvature, as impedances may be higher at each end of catheter 12 and lower towards the central portion of catheter 12. The change in impedance of an electrode 34 as it progresses through the patient's vessels can provide information about the location of that electrode 34. In addition, the differences in impedances of electrodes 34 along the length of catheter 12 may provide information about the placement of catheter 12.

In one example, catheter 12 may be placed in a vessel that varies in diameter, with distal electrodes 34 resting in a desired vessel (e.g., in superior vena cava 24). The impedances of different, more proximal electrodes would be expected to vary depending on their position in the venous system. In one example, catheter 12, when placed in a desired position, would be expected to include: 1) electrodes 34 whose impedances are reduced as the electrodes 34 approach the wall of a vessel (e.g., superior vena cava 24); and 2) electrodes 34 having impedance profiles with a desired shape. In one example, measured impedances may be compared to impedance thresholds or profiles stored in data storage 79, to determine if one or more electrodes 34 are properly placed.

In another example, the impedances of distal electrodes can be compared to the impedances of proximal electrodes as the catheter 12 is advanced through superior vena cava 24 towards the atrium. As the distal electrodes enter the atrium, the difference between the distal and proximal impedance measurements may exceed a predetermined threshold allowing the system 10 to provide an indication to the operator. Catheter 12 can then be withdrawn (or advanced depending on the application) to the desired location. Signal filtering, processing, and analytical techniques known in the art can be used to assess the impedance measurements in real time.

A catheter 12 that is under-inserted may have few or no electrodes 34 resting in the desired vessel (e.g., superior vena cava 24), which would result in electrode impedance profiles having different shapes than the desired shape. In addition, a catheter 12 that is over-inserted may have one or more electrodes 34 that are close to, or in contact with, the atrium, which may also result in impedance profiles having different shapes than the desired shape. In one example, the impedance of one or more electrodes 34 is monitored as catheter 12 is inserted into the patient and electrodes 34 move through the patient's venous system. Changes in the impedance profiles can be displayed to the health professional performing the insertion, and the impedance profiles can be used to confirm proper placement of catheter 12.

In one example, a method for positioning intravascular catheter 12 may include positioning catheter 12 in a first position in a venous system of a patient, wherein catheter 12 includes a plurality of electrodes 34, and each electrode 34 of the plurality of electrodes 34 is configured to emit electrical signals to stimulate a phrenic nerve; measuring an impedance between a first electrode 34 of the plurality of electrodes 34 and a second electrode; and based on the measured impedance, adjusting catheter 12 to a second position different from the first position.

In other examples, catheter 12 may include a strain gauge and/or an accelerometer (not shown). Either the strain gauge or the accelerometer may be placed at or near the distal end of catheter 12, in one of the lumens. The strain gauge could detect flex in a distal portion of catheter 12, and the accelerometer could detect movement/acceleration of the distal portion of catheter 12. Information from the strain gauge and/or accelerometer could be used to determine whether the distal end of catheter 12 is in the atrium (e.g., heartbeats may cause movement of the distal end of catheter 12). The strain gauge or the accelerometer could be an integral, permanent part of catheter 12 or could be positioned in a lumen of catheter 12 temporarily during positioning of catheter 12.

Electrode Selection and Determining Stimulation Parameters

Nerve signals acquired by sensing electrodes 34 may be used to select electrodes 34 for nerve stimulation. Electrodes 34 that are closer to a target nerve may sense nerve activity having a higher amplitude, while electrodes 34 that are farther from a target nerve may sense nerve activity having a lower amplitude. If a greater diaphragm response is desired, electrodes 34 that are closer to the nerve, as determined based on received nerve activity signals, may be selected for nerve stimulation. In other cases, if less diaphragm response is desired, electrodes 34 that are farther from the nerve, as determined based on received nerve activity signals, may be selected for nerve stimulation.

Typical nerve signals for, e.g., phrenic nerves, follow a pattern that has distinct characteristics (e.g., spectral characteristics and modulation over time). To select electrodes 34 for nerve stimulation, the sensed nerve signals from different electrodes 34 can be analyzed for their spectral and temporal characteristics. Of electrodes 34 having sensed signal patterns matching typical phrenic nerve activity, the optimal electrodes 34 can be selected based on the amplitude of the signal and how strongly the signal correlates to the typical pattern. In one example, a fast Fourier transform can be used to provide a correlation factor to a reference signal in near real-time. In another example, the sensed signals can be frequency filtered in the frequency range of interest, based on the typical characteristics of the phrenic nerve signal, and then analyzed over time to observe periods or bursts of activity in the frequency range of interest.

In one example, a method for selecting one or more electrodes for nerve stimulation may include inserting intravascular catheter 12 into: a) at least one of left subclavian vein 22 or left jugular vein 32, and b) superior vena cava 24, wherein catheter 12 includes a plurality of electrodes 34, and each electrode 34 of the plurality of electrodes 34 is configured to emit electrical signals to stimulate a nerve; using one or more electrodes 34 of the plurality of electrodes 34 to acquire an electrical signal emitted from the nerve; based on the acquired electrical signal, selecting an electrode 34 or an electrode combination for a nerve stimulation; and using the selected electrode 34 or electrode combination, stimulating the nerve.

The processed nerve activity waveforms additionally may be used to determine parameters for nerve stimulation. The processed waveforms may provide information regarding intrinsic breath rate (e.g., if the patient is attempting to breathe on his/her own) and nerve signal amplitude. The stimulation parameters may be adjusted based on the breath rate of previous stimulated breaths (e.g., to increase or decrease the breath rate, as sensed by the sensing electrodes) and nerve activity resulting from stimulation during previous breaths (e.g., to increase or decrease the strength of stimulation). Various parameters that may be adjusted include stimulation pulse amplitude, stimulation pulse width, stimulation pulse frequency, stimulation duration, and the interval between stimulations/pulse trains (e.g., stimulated breath rate). Accordingly, sensed nerve activity signals may be used to determine and adjust the nerve stimulation parameters in a closed-loop system.

Impedance information may be used to determine a breath rate of the patient in order to adjust nerve stimulation parameters (e.g., stimulation pulse amplitude, stimulation pulse width, stimulation pulse frequency, stimulation duration, and the interval between stimulations/pulse trains (e.g., stimulated breath rate)). Electrical impedance of lung tissue changes as a function of air content. Accordingly, the electrical impedance of the thorax changes during inhalation and exhalation. The thorax presents an electrical impedance that includes two components: a relatively constant value and a varying value. Changes in impedance may result from the following two effects during inspiration: 1) there is an increase in the gas volume of the chest in relation to the fluid volume, which may cause conductivity to decrease, and 2) the length of the conductance path (e.g., between two electrodes) increases when the lungs expand. These effects may cause impedance to increase during inspiration. There is an approximately linear correlation between the impedance changes and the volume of respirated air. The varying component of impedance (i.e., respiratory impedance) generates a varying voltage component when current is injected (e.g., by electrodes 34). This varying voltage component can then be used to determine the person's breathing rate.

Information from blood gas sensor 62 may be used by a health professional, or by controller 64, to adjust stimulation parameters. For example, if blood $O_2$ levels are low (or blood $CO_2$ levels are high) controller 64 may send a signal to electrodes 34 to emit stimulation signals having a higher charge (amplitude×pulse width) or frequency, and may stimulate a sigh breath. Conversely, if blood $O_2$ levels are high (or blood $CO_2$ levels are low), controller 64 may cause electrodes 34 to emit stimulation signals having a lower charge or frequency. Based on information from blood gas sensor 62, the following parameters can be adjusted: stimulation pulse amplitude, stimulation pulse width, stimulation pulse frequency, stimulation duration, and the interval between stimulations/pulse trains (e.g., stimulated breath rate).

For any of the parameter adjustments described herein, increasing stimulation pulse amplitude, width and/or frequency may increase lung volume during a stimulated breath. Increasing stimulation duration may increase lung volume and/or increase the amount of time air remains in the lungs during a stimulated breath, allowing for an extended gas exchange period. Increasing the stimulated breath rate may allow for additional gas exchange periods over a given period of time, which may increase the amount and/or speed of gas exchange.

The system 10 and catheter 12 described herein may include any combination of sensing features. For example, catheter 12 may be configured to sense ECG, impedance, nerve activity, blood gas levels, and CVP, and the system 10 may be configured to position catheter 12, select electrodes 34 for stimulation, and select stimulation parameters based on one or more types of information received by sensors or electrodes 34.

Accordingly, the various visualization and sensing functions of system 10 may assist a user in one or more of positioning a transvascular catheter, selecting optimal electrodes for nerve stimulation, or selecting or adjusting parameters for nerve stimulation.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method of electrical stimulation, the method comprising:
   delivering a first electrical stimulation signal to a nerve, wherein delivering the first electrical stimulation signal to the nerve results in a lung lobe having a first volume;
   after delivering the first electrical stimulation signal, measuring an impedance of a portion of an anatomy proximate a blood vessel;
   determining a second stimulation signal based on the measured impedance; and
   delivering the second stimulation signal to the nerve, wherein the nerve is proximate the blood vessel, wherein delivering the second electrical stimulation signal to the nerve results in the lung lobe having a second lung volume, and wherein the second volume is greater than the first volume.

2. The method of claim 1, wherein the first stimulation signal, the second stimulation signal, or both, is an electrical stimulation signal.

3. The method of claim 2, wherein the electrical stimulation signal is delivered via an electrode positioned in the blood vessel.

4. The method of claim 1, wherein the portion of the anatomy includes a space between a first lung tissue and a second lung tissue.

5. The method of claim 1, wherein the nerve is a phrenic nerve.

6. The method of claim 1, wherein:
the first electrical stimulation signal includes a first pulse amplitude, a first pulse width, a first pulse frequency, a first stimulation duration, and a first interval between stimulations;
the second electrical stimulation signal includes a second pulse amplitude, a second pulse width, a second pulse frequency, a second stimulation duration, and a second interval between stimulations; and
the first pulse amplitude is different than the second pulse amplitude, the first pulse width is different than the second pulse width, the first pulse frequency is different than the second pulse frequency, the first stimulation duration is different than the second stimulation duration; and/or the first interval between stimulations is different than the second interval between stimulations.

7. The method of claim 1, wherein the measured impedance is a first impedance, and the method further comprises, after delivering the second stimulation signal:
measuring a second impedance of the portion of the anatomy, wherein the first impedance is different than the second impedance.

8. A method of electrical stimulation, the method comprising:
measuring a first impedance of tissue;
based on the impedance measurement, determining a first breath characteristic,
based on the first breath characteristic, determining one or more parameters of a stimulation signal;
delivering the stimulation signal to a nerve;
measuring a second impedance of tissue; and
based on the second impedance, determining a second breath characteristic;
wherein the first breath characteristic includes a volume of a first portion of a lung, and the second breath characteristic includes a volume of a second portion of the lung.

9. The method of claim 8, wherein the tissue is located in a thorax.

10. The method of claim 8, further comprising:
positioning an electrode in a blood vessel, wherein delivering the first stimulation signal, the second stimulation signal, or both, includes delivering an electrical stimulation signal via the electrode.

11. The method of claim 8, wherein the first breath characteristic, the second breath characteristic, or both, includes an airway volume and/or an airway pressure.

12. The method of claim 8, wherein the first breath characteristic is a first volume of the first portion of the lung, the second breath characteristic is a first volume of the second portion of the lung, and the method further comprises, after delivering the stimulation signal to a nerve:
measuring a third impedance of tissue;
based on the third impedance, calculating a second volume of the first portion of the lung;
measuring a fourth impedance of tissue; and
based on the fourth impedance, calculating a second volume of the second portion of the lung;
wherein the first volume of the first portion of the lung is different than the second volume of the first portion of the lung; and
the first volume of the second portion of the lung is different than the second volume of the second portion of the lung.

13. A method of electrical stimulation, the method comprising:
delivering a first electrical stimulation signal comprising a first pulse width to a nerve;
measuring a first impedance of lung tissue;
calculating a first lung volume based on the first impedance;
based on the first lung volume, calculating a second electrical stimulation signal comprising a second pulse width, wherein the second pulse width is greater than the first pulse width; and
delivering the second electrical stimulation signal to the nerve.

14. The method of claim 13, further comprising:
measuring a second impedance of lung tissue; and
calculating a second lung volume based on the second impedance, wherein the second lung volume is greater than the first lung volume.

15. The method of claim 13, wherein the lung volume is a volume of a lower lung lobe.

16. The method of claim 13, wherein the lung tissue is lung tissue of a patient, and the patient is receiving breathing assistance from a mechanical ventilator.

17. The method of claim 14, wherein the first impedance measurement and the second impedance measurement are both taken during an inspiration.

* * * * *